United States Patent [19]
Templin et al.

[11] Patent Number: 5,646,048
[45] Date of Patent: Jul. 8, 1997

[54] MICROCOLUMNAR ANALYTICAL APPARATUS WITH MICROCOLUMNAR FLOW GATING INTERFACE AND METHOD OF USING THE APPARATUS

[75] Inventors: Catherine Keely Templin, Los Altos; Douglass McManigill, Palo Alto, both of Calif.

[73] Assignee: Hewlett-Packard Company, Palo Alto, Calif.

[21] Appl. No.: 505,941

[22] Filed: Jul. 24, 1995

[51] Int. Cl.$^6$ .................. G01N 1/10; G01N 30/02; B01D 15/08
[52] U.S. Cl. .................. 436/180; 96/106; 204/601; 210/198.2; 285/911; 422/70; 422/103
[58] Field of Search .................. 210/95, 198.2, 210/656, 659; 204/601; 96/104, 106; 422/69, 70, 103, 104; 436/161, 180; 285/177, 911, 382, 382.1, 382.2, 382.7

[56] References Cited

U.S. PATENT DOCUMENTS

| | | | |
|---|---|---|---|
| 3,936,374 | 2/1976 | Bradley et al. | 96/106 |
| 4,453,954 | 6/1984 | Kolb et al. | 210/198.2 |
| 4,662,914 | 5/1987 | Hansen et al. | 96/106 |
| 4,676,897 | 6/1987 | Kuze et al. | 210/198.2 |
| 4,708,782 | 11/1987 | Andresen et al. | |
| 5,131,998 | 7/1992 | Jorgenson et al. | |
| 5,326,445 | 7/1994 | Lauer et al. | |
| 5,389,221 | 2/1995 | Jorgenson . | |
| 5,494,641 | 2/1996 | Krstanovic et al. | 96/106 |
| 5,500,071 | 3/1996 | Kaltenbach et al. | 210/198.2 |

OTHER PUBLICATIONS

Bushey, Michelle M., et al., Anal. Chem., "Automated Instrumentation for Comprehensive . . . ", 1990, 62, pp. 161–167, 978–984.

Lemmo, Anthony V., et al., Anal. Chem., "Transverse Flow Gating Interface . . . ", 1993, 65, pp. 1576–1581.

*Primary Examiner*—Joseph W. Drodge

[57] ABSTRACT

A microcolumnar analytical apparatus having a flow gating interface system for interfacing a first microcolumn and a second microcolumn is provided. The apparatus includes a flow gating interface, a first fluid conduit (e.g. a liquid chromatograph microcolumn) of a fluid sample, a flush liquid supplier, and a second fluid conduit (e.g. a capillary electrophoresis microcolumn) for analysis of the effluent fluid sample from the first fluid conduit. The flow gating interface includes a first microcolumnar section, a second microcolumnar section, and a channel. The channel, having an inwardly facing wall, encloses at least a portion each of the first microcolumnar section and the second microcolumnar section for conducting a flush fluid flow past the outlet end of the first microcolumnar section and the inlet end of the second microcolumnar section. The inwardly facing wall of the channel nonfixedly constrains and aligns said end portions of the first and second microcolumnar section due to the relative curvature and elasticity of the microcolumnar sections and the channel. The first fluid conduct is connected to and in fluid communication with the first microcolumnar section of the flow gating interface. The second fluid conducting means has a microcolumn. This microcolumn is connected to and in fluid communication with the second microcolumnar section of the flow gating interface. The flush liquid supplier is connected to and in fluid communication with the channel.

28 Claims, 9 Drawing Sheets

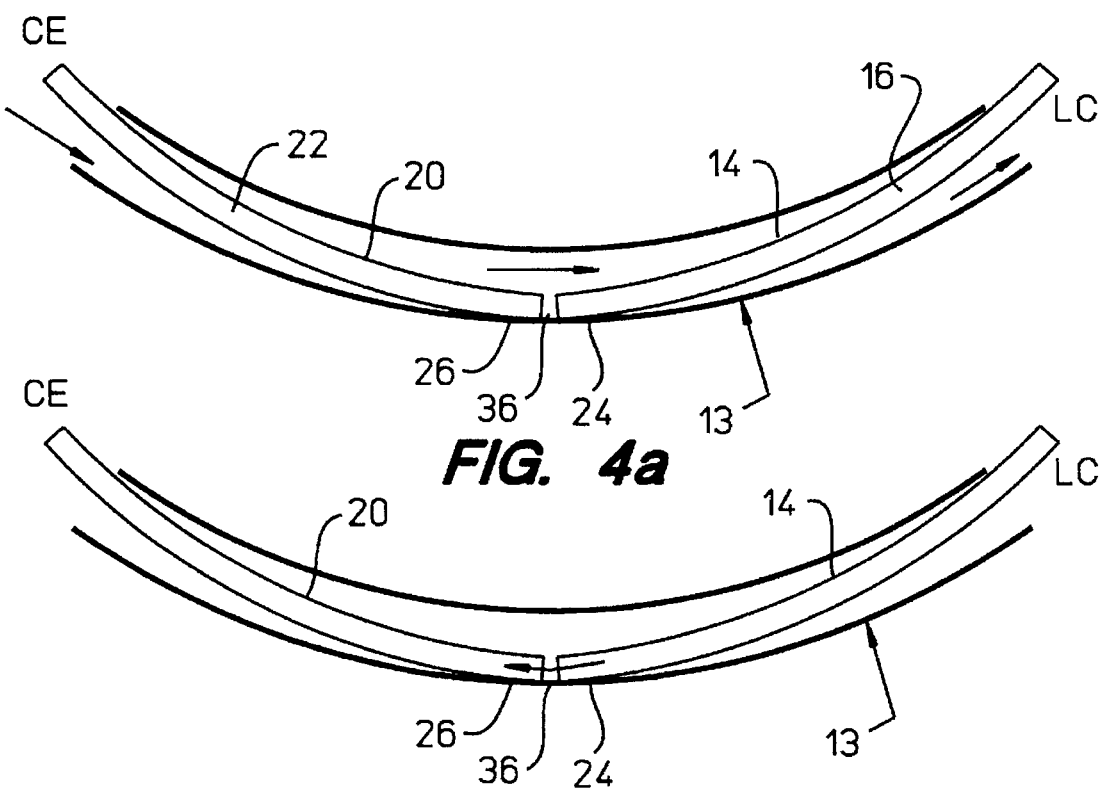
FIG. 4a
FIG. 4b
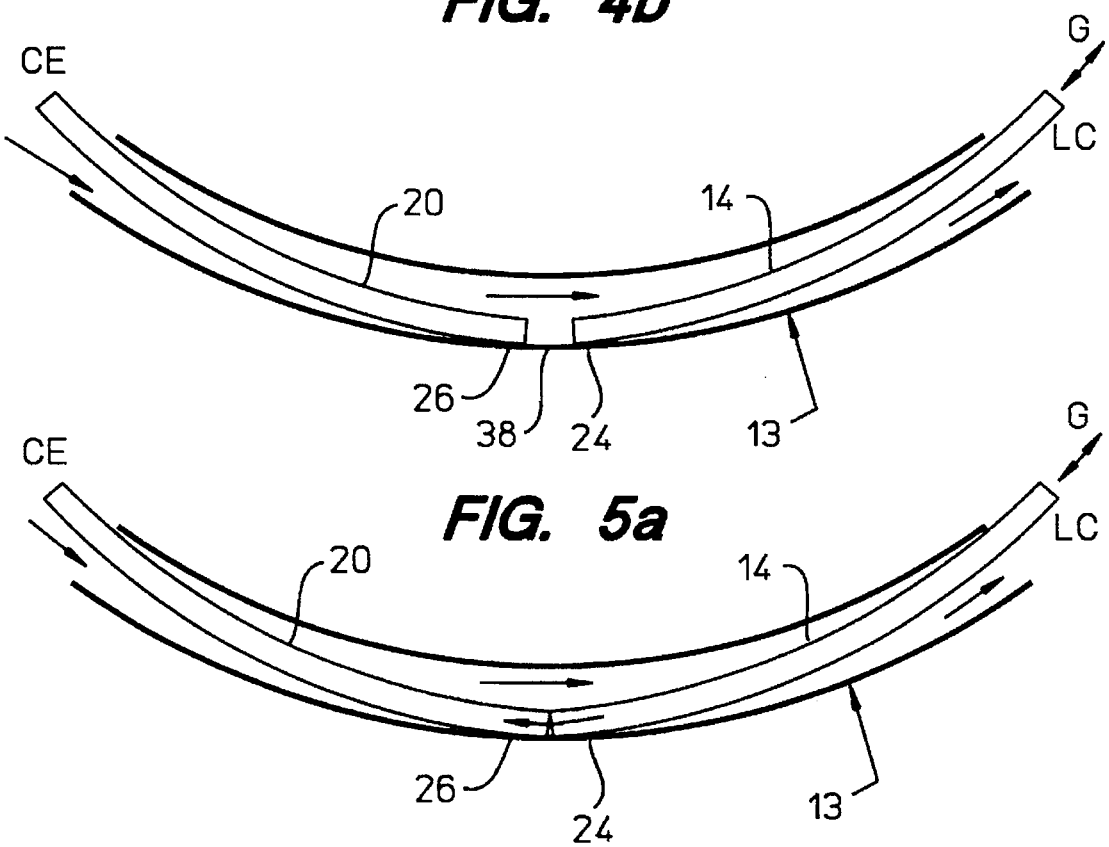
FIG. 5a
FIG. 5b

MICROCOLUMNAR ANALYTICAL APPARATUS WITH MICROCOLUMNAR FLOW GATING INTERFACE AND METHOD OF USING THE APPARATUS

FIELD OF THE INVENTION

The present invention relates to an analytical apparatus and method involving a flow gating interface for coupling flow from a first fluid conducting device to a second fluid conducting device which is an analytical device, wherein a microcolumn is involved. More particularly, this invention relates to an analytical apparatus and method involving a flow gating interface for coupling flow from a microcolumn of a first microcolumnar device to a microcolumn of a second microcolumnar device of separation means.

BACKGROUND

In the identification or quantification of analytes in a sample, often more than one analytical technique is needed to adequately separate the analytes. These techniques generally differ from one another based on the difference in various properties of the analytes. For example, one separation technique may be based on the molecular size of the analytes and another technique may be based on the electrical charge to mass ratios of the analytes. Analytical methods that separate the analytes based on two different analytical techniques are sometimes referred to as "two-dimensional" methods. Analytical techniques suitable for application in separating analytes in liquid samples include, for example, liquid chromatography, electrophoresis, and the like.

Recently, analytical techniques that employ small tubular structures (i.e., microcolumns) have gained wide acceptance. For example, high performance liquid chromatography (HPLC) and capillary electrophoresis (CE) are commonly used techniques for separating analytes, including macromolecules and biomolecules such as proteins, nucleic acids, DNA molecules and fragments, carbohydrates, fatty acids, peptides, and the like. In these systems, a sample that is suspected of containing analytes is sent through a microcolumn. As the molecules in the sample migrate through the microcolumn, depending on the interaction of the analytes with the other substances (such as packing material) in the microcolumn, the analytes separate from one another. Although it is practicable to collect fractions of the liquid exiting a microcolumn and process them through another microcolumn, it is more convenient to couple the microcolumns for fluid transfer. This can obviate the need to collect fractions from one microcolumn and then inject them into another one.

To transfer only portions of a fluid exiting from a microcolumn to another microcolumn, a well designed interface system is important for properly coupling the microcolumns so that the desired liquid portions are transferred without excessive loss. Systems for interfacing a first microcolumn to a second microcolumn have been introduced to enable switching between moving fluid from a first microcolumn and moving fluid from a flush buffer supply to a second microcolumn. For example, U.S. Pat. No. 5,131,991 (Jorgenson et al.) discloses utilizing a valve means connecting the capillary inlet end of a two-dimensional separation system to the chromatography column outlet and to a buffer supply means. The valve means is switchable between a first configuration providing fluid to the capillary inlet end from the buffer supply means and a second configuration providing fluid to the capillary inlet end from the chromatography column. However, in this system, a relatively expensive and sophisticated valve mechanism is needed for switching between the first and the second configurations.

U.S. Pat. No. 5,389,221 (Jorgenson et al.) discloses a combination liquid chromatography and capillary electrophoresis separation system having a flow gating interface. The flow gating interface has an effluent channel and a gating channel (which is shown in FIGS. 1a and 1b). The gating channel 2 transversely intersects the effluent channel 3. Arrows C and D show the flow directions of the gating channel 2 and of the effluent channel 3 respectively. The channel is formed by two plates 4A, 4B stacked together, separated by a gasket (not shown in the drawing) which has a channel cut from it. A liquid chromatography column 5A is connected to the effluent channel 3 upstream portion and an electrophoresis capillary 5B is connected to the effluent channel downstream portion. A flush solution inlet line is connected to the gating channel 2 upstream portion and the flush solution outlet line is connected to the gating channel downstream portion. A valve (not shown in FIGS. 1a and 1b) regulates the flow of flushed solution from the flush solution inlet line to the gating channel upstream portion. The intersection portion is configured so that the rate of flow of the effluent from the effluent channel upstream portion to the effluent channel downstream portion decreases as the rate of flush flow in the gating channel increases. In this system, since plates and gaskets need to be assembled, the manufacturing process is relatively complex. Because precise positioning of the outlet end of the liquid chromatography column and the inlet end of the electrophoresis capillary is important, extensive skill is required to cut the gasket, make the plates, and align the plates with the gasket, the chromatography column, and the capillary. What is needed is a relatively simple and inexpensive flow gating interface. Also needed is a two-dimensional microcolumnar separation apparatus having such a flow gating interface.

SUMMARY

The present invention provides a microcolumnar analytical apparatus having a flow gating interface system for interfacing a fluid conduit with a fluid conducting analytical device. The apparatus includes a flow gating interface of the present invention, a first fluid conducting means for transferring a fluid sample, a flush liquid supply means, and a second fluid conducting means for analysis of the effluent fluid sample from the first fluid conducting means. The second fluid conducting means has a microcolumn. The flush liquid supply means is operatively connected to and in fluid communication with a channel of the flow gating interface.

The flow gating interface provided in the present invention includes a first microcolumnar section, a second microcolumnar section, and a channel, each of which has a center line. The first microcolumnar section has an outlet end portion having an outlet end and a lumen for conducting a fluid flow. The first fluid conducting means is operatively connected to and in fluid communication with the first microcolumnar section of the flow gating interface. The second microcolumnar section has an inlet end portion having an inlet end and a lumen for conducting a fluid flow. The second fluid conducting means is operatively connected to and in fluid communication with the second microcolumnar section of the flow gating interface. The channel, having an inwardly facing wall, encloses at least a portion each of the first microcolumnar section and the second microcolumnar section for conducting a flush fluid flow past the outlet end of the first microcolumnar section and the inlet end of the second microcolumnar section. The inwardly facing wall of the channel nonfixedly constrains and aligns the end portions of the first and second microcolumnar sections. This can facilitate the transfer of fluid from the first microcolumnar section to the second microcolumnar section when desired. As used herein, the term "channel" refers to a conduit having a length larger than the perimeter of the cross sectional area perpendicular to the center line.

In one aspect of the invention, the inwardly facing wall slidably constrains the end portions of the first and second microcolumnar section. The flow gating interface can further have a means for reciprocatively moving at least one of the microcolumnar sections to alternatively decrease and increase the distance between the interfacing ends of the microcolumnar sections.

In another aspect of the invention, in the flow gating interface, the channel is bent to facilitate constraining the end portions of the first and second microcolumnar sections.

The present invention further provides a method for analyzing a liquid sample. The method includes transferring the sample thorough a first microcolumnar device which includes a first microcolumn; coupling the first microcolumn to a second microcolumn which is part of a second microcolumnar device to control fluid flow from the first microcolumn to the second microcolumn; and analyzing the fluid transferred from the first microcolumnar device to the second microcolumnar device. The coupling and fluid flow-controlling process includes: using the inwardly facing wall of a channel to nonfixedly constrain an outlet end portion of a first microcolumnar section and an inlet end portion of a second microcolumnar section; substantially preventing transfer of fluid from the first microcolumnar section to the second microcolumnar section by flushing a flush fluid in the channel through a gap between the outlet end of the first microcolumnar section and the inlet end of the second microcolumnar section; and transferring fluid from the first microcolumnar section to the second microcolumnar section by reducing the amount of fluid exiting the outlet end from being carried away by the flush fluid. In this method, the first microcolumnar section is operatively connected to and in fluid communication with the first microcolumn. The second microcolumnar section is operatively connected to and in fluid communication with the second microcolumn. The outlet end of the outlet end portion is proximate the inlet end of the inlet end portion. The center lines of the outlet end portion and inlet end portion are substantially parallel to facilitate the transfer of fluid from the outlet end of first microcolumnar section to the inlet end of the second microcolumnar section when desired. The channel is adapted to conduct a flush fluid flow.

A method of making an analytical apparatus for analyzing a liquid sample is further provided. The method includes the steps of providing a first fluid conducting means for transferring the fluid sample; providing a second fluid conducting means for analysis of an effluent fluid sample from the first fluid conducting means; coupling the first fluid conducing means to a microcolumn of the second fluid conducting means with a flow gating interface having a channel to control fluid flow from the first fluid conducting means to the second fluid conducting means; and connecting a flush liquid supply means operatively to and in fluid communication with the channel for flowing the flush fluid through the channel. This flow gating interface includes a first microcolumnar section, a second microcolumnar section, and a channel, each of which has a center line. The first microcolumnar section has an outlet end portion having an outlet end and a lumen for conducting a fluid flow. The second microcolumnar section has an inlet end portion having an inlet end and a lumen for conducting a fluid flow. In this method, the first microcolumnar section is operatively connected to and in fluid communication with the first fluid conducting means. The second microcolumnar section is operatively connected to and in fluid communication with the microcolumn of the second fluid conducting means. The channel, having inwardly facing walls, encloses at least a portion each of the first microcolumnar section and the second microcolumnar section for conducting a flush fluid flow past the outlet end of the first microcolumnar section and the inlet end of the second microcolumnar section. The inwardly facing wall of the channel nonfixedly constrains and aligns the end portions of the first and second microcolumnar sections such that the outlet end of the first microcolumnar section is proximate the inlet end of the second microcolumnar section. The center lines of the outlet end portion and the inlet end portion are generally parallel to facilitate the transfer of fluid from the outlet end of first microcolumnar section to the inlet end of the second microcolumnar section when desired.

The flow gating interface of the present invention enables precise control of transfer of a fluid from a microcolumn into another microcolumn. Such transfer can be done for relatively large volumes, as well as very small volumes of fluids, for example, even for samples as small as 10 picoliters. Such capability for small volume sampling will be useful in the investigation (chemical analysis) of, for example, single cells. In one embodiment, the end portions of the microcolumnar sections are flexible and not fixedly attached to the channel and the channel is so shaped such that, when the microcolumnar sections are withdrawn and then repositioned to achieve the original configuration, they self align.

The analytical apparatus of the present invention can be advantageously employed to analyze samples efficiently using two-dimensional analyses. Because of the simplicity of construction of the flow gating interface, the present invention is particularly adaptable for conducting analysis wherein various combinations of orthogonal analytical techniques are evaluated. In one aspect of the flow gating interface of the present invention, the curved or angular shape of the inwardly facing (or lumenal) wall of the channel (or conduit) naturally guides the flexible microcolumnar sections so that two such interfacing sections can be aligned in a substantially collinear fashion without radial adjustment. This greatly simplifies the aligning process over prior art interfacing methods. Further, because the position where the microcolumnar section is mechanically affixed to the channel and the concentricity of the microcolumnar sections and the channel at locations distal to the interfacing ends are not important, effective sealing can be readily achieved to reduce the risk of leaks. Because the interfacing end portions are not attached to (i.e., they are detachable from) the channel, the microcolumnar sections can easily be removed from the channel for replacement of the microcolumns. Since the center lines of the microcolumnar sections are generally parallel with that of the channel, the determination of position of the microcolumnar sections in the channel by visual inspection, or by imaging techniques such as ultrasound, is facilitated.

In another aspect of the invention, slidable movement of the microcolumnar section can also be used to reduce unwanted transfer of fluid from one microcolumnar section to another. Such microcolumn movement (e.g., by using a solenoid to drive the movement) can be done at a higher rate than the stopping of the flush fluid flow (as is done in prior art). By placing the interfacing ends of the microcolumnar sections in an abutting position, the dilution of samples introduced into the second microcolumnar separation means can be greatly reduced. The electrodes for capillary electrophoresis can be located relatively far from the interfacing ends of the microcolumnar sections, thus reducing the risk of introducing bubbles formed by electrolysis into the microcolumns. If one or more microcolumnar sections are slidably moved, flush fluid flow need not be stopped by controlling the flush fluid pump. This eliminates the problem of fluid shock and compliance in the channel and related flow conducting parts.

BRIEF DESCRIPTION OF THE DRAWING

The following figures which show the embodiments of the present invention are included to better illustrate the microcolumnar analytical apparatus of the present invention. In these figures, wherein like numerals represent like features in the several views:

FIG. 1b shows a different fluid flow pattern in the prior art flow gating interface of FIG. 1a;

FIG. 4a is a plan view of the flow gating interface of FIG. 3 in portion;

FIG. 4b is a plan view of the flow gating interface of FIG. 3 in portion showing the transfer of fluid from a first microcolumnar section to a second microcolumnar section;

FIG. 5a is a plan view of another embodiment of a flow gating interface in portion according to the present invention;

FIG. 5b is a plan view of the flow gating interface of FIG. 5a showing the transfer of fluid from the first microcolumnar section to the second microcolumnar section;

FIG. 6 is a sectional view along the length of the channel of a portion of the flow gating interface of FIG. 5a;

DETAILED DESCRIPTION OF THE INVENTION

The flow gating interface of the present invention has a channel for conducting a flush fluid flow and the inwardly facing wall of the channel constrains the first and second microcolumnar sections such that the interfacing end portions of these sections are proximate to each other and are substantially parallel. The end portions of the microcolumnar sections are not fixedly attached to the wall of the channel. This flow gating interface can be used for interfacing two fluid conduits (e.g., microcolumns) in a system wherein only intermittent transfer of fluid from one fluid condiut to the other is desired. To illustrate the application of the flow gating interface, an embodiment of a microcolumnar analytical apparatus of the present invention having such a flow gating interface for interfacing a first microcolumn and a second microcolumn is described.

Figure 1A:
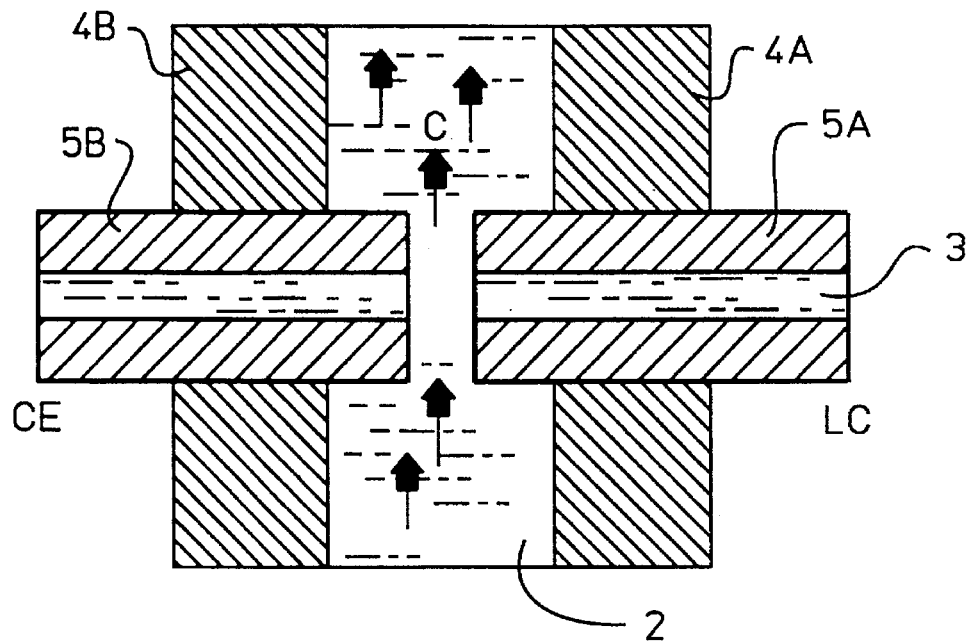
FIG. 1a shows a schematic representation of a prior art flow gating interface.
Figure 1B:
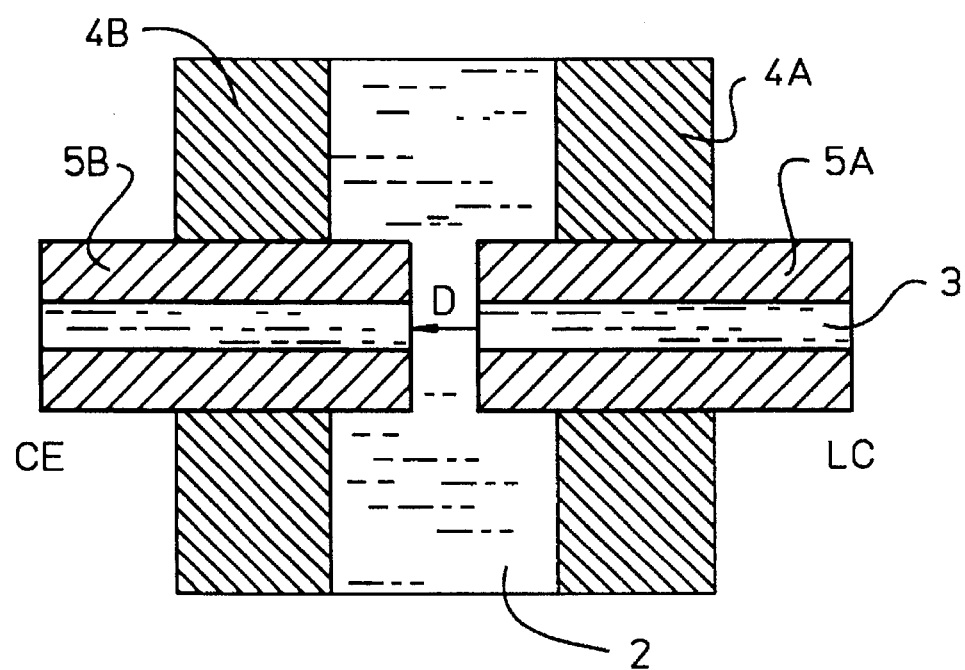
Figure 2:
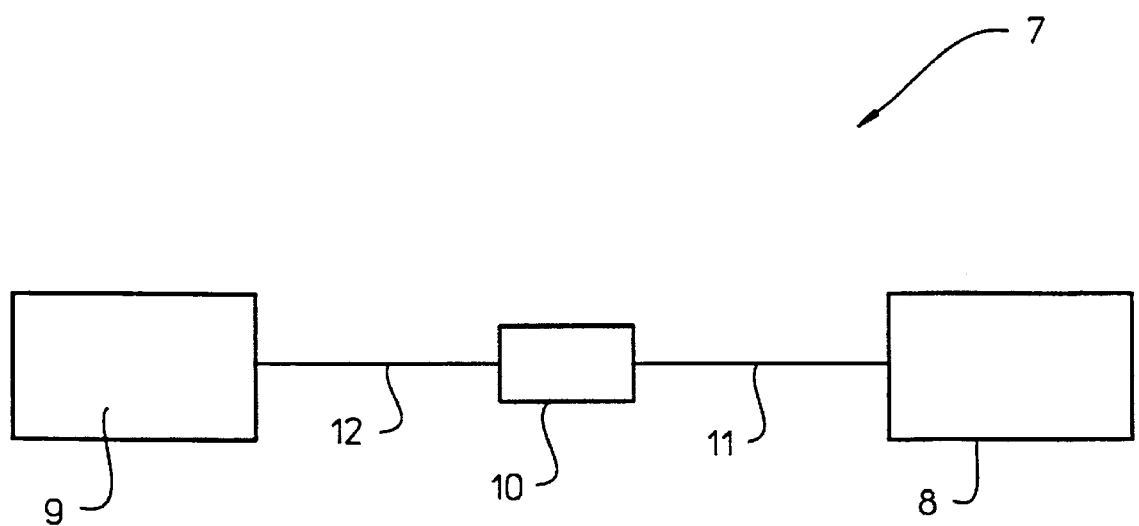
FIG. 2 shows a schematic representation of a microcolumnar analytical apparatus according to the present invention.

FIG. 2 illustrates a preferred embodiment wherein the flow gating interface system of the present invention interfaces two devices each with microcolumns (e.g., LC and CE). Referring to FIG. 2, the microcolumnar analytical apparatus 7 according to the present invention has a first fluid conducting (or conduit) means (preferably a microcolumnar means for separation or analysis) 8 interfacing with a second fluid conducting means (preferably a microcolumnar means for separation or analysis) 9 by a flow gating interface 10. The flow gating interface couples (i.e., interfaces) a microcolumn 11 from the first conducting conduit (preferably microcolumnar separation) means 8 to a microcolumn 12 from the second fluid conducting (preferably microcolumnar separation) means 9. The flow gating interface 10 can be controlled so that fluid exiting the microcolumn 11 is transferred into microcolumn 12 when desired.

Preferably, the separation techniques of first fluid conducting means 8 and the second fluid conducting means 9 are selected such that the techniques of separation in these two separation means are orthogonal to each other (i.e., the separation in the two techniques are based on different properties of the sample). This results in a "two dimensional (2D) analysis."

The First Fluid Conducting Means

The first fluid conducting means coupled to the flow gating interface of the present invention can be any means by which a fluid is conducted through a microcolumn. In fact, it need not perform any separation function but merely transfers fluid through a conduit. It may even be merely a container, not necessarily column-shaped, as long as fluid can be conducted out of it into the flow gating interface of the present invention. In the embodiment of FIG. 2, the first fluid conducting means can be any device with a fluid conduit. Preferably, it can be a separation means (referred to as the first microcolumnar separation means herein) using a microcolumn for separating analytes in a liquid sample, such as in liquid chromatography (LC) or capillary electrophoresis (CE), e.g., capillary zone electrophoresis (CZE). An important factor for the selection of the first and the second fluid conducting means in chemical analysis is that the liquid exiting the microcolumn of the first microcolumnar separation means can be transferred to the second fluid conducting means (e.g., a microcolumn of a second microcolumnar separation means) in a confined environment. Preferably, the first microcolumnar separation means is a liquid chromatography system because generally the flow in a liquid chromatographic column is driven by hydrostatic pressure.

A particularly useful type of liquid chromatograph suitable for the present invention is high performance liquid chromatograph (HPLC). However, any microcolumnar separation means that utilizes an analytical microcolumn for separating different target analytes in a liquid sample can also be used. Examples of chromatography techniques practicable for such microcolumnar separation include reverse phase chromatography, size exclusion chromatography, adsorption chromatography, affinity chromatography, ion exchange chromatography, and the like. Liquid chromatography and high performance liquid chromatography, as well as the equipment for such techniques are generally known in art. For example, U.S. Pat. No. 5,131,998 (Jorgenson et al.), U.S. Pat. No. 5,389,221 (Jorgenson et al.) disclose liquid chromatography equipment and methods for two-dimensional separation systems (said disclosures of equipment and method are incorporated by reference herein).

Generally, the liquid chromatography system in the analytical apparatus of the present invention has a microcolumn that contains a packing or separating medium or matrix. After a sample is introduced into the microcolumn, an elution fluid is driven through the microcolumn to elute and separate the analytes in the sample. Separation is dependent on the particular properties of the analytes affecting the interaction of the analytes with the packing material. For example, the separation of analytes by the microcolumn can be based on the molecular size of the analytes, which affects the speed of passage through the intermolecular space of the packing material in size exclusion chromatography. The dimensions of the microcolumn are dependent on the separation technique selected and the resolution desired. Thus, the length, inside diameter (i.d.), and outside diameter (o.d.) of the microcolumn is dependent on the technique of the liquid chromatography and the resolution in the separation. The first microcolumnar separation means of the present invention has a microcolumn having a typical inside diameter (i.d.) of about 10 µm, to about 5000 µm, preferably about 100 µm to about 2000 µm. The o.d. of the microcolumn is generally selected such that the microcolumn has the mechanical strength and integrity to allow operation with the appropriate pressure and the necessary manipulation. For example, the o.d. of a microcolumn for HPLC is typically about 400 µm to about 10 mm.

Additionally, the first microcolumnar separation means can also have a reservoir containing a buffer solution or other flushing fluid for the operation of the liquid chromatograph after a sample of analytes has been introduced into the microcolumn. The material of construction of the microcolumn is dependent on the type of liquid chromatography used. The selection of the material is affected by the pressure exerted in the microcolumn and the chemical resistance desired. Commonly available microcolumns can be made of metal (e.g., stainless steel), nonmetallic inorganic material (e.g., fused silica), as well as polymer such as polytetrafluoroethylene (PTFE), polyether ether ketone (PEEK), and the like. The selection of the dimensions and material of construction of the microcolumns for separation means such as liquid chromatography and capillary electrophoresis are known in the art.

The Second Fluid Conducting means

The second fluid conducting means that can be coupled with the first fluid conducting means by the flow gating interface of the present invention can be any device (preferably an analytical device having a microcolumn) through which a fluid can be passed. As in the first fluid conducting means, the second fluid conducting means can also be merely a fluid container. If it is an analytical device having an analytical microcolumn, the second fluid conducting means is referred to as the second microcolumnar separation means herein. In an analytical apparatus wherein the first and the second fluid conducting means are separation means, as previously stated, it is preferred that the first microcolumnar separation means and the second microcolumnar separation means are based on orthogonal separation techniques. The more different the properties that are the basis of separation in the two techniques (i.e., the more orthogonal), the better will be the separation result of the two-dimensional separation system. Generally, it has been found that liquid chromatography systems, such as size exclusion chromatography, reverse phase chromatography, and the like, can be used in series with capillary electrophoresis to facilitate the separation of analytes in a sample. The flexibility of capillary electrophoresis with size exclusion chromatography in reverse phase chromatography makes such systems particularly adaptable for two-dimensional separation. Capillary electrophoresis systems and methods are well known in the art. For example, CZE systems and methods of operation have been disclosed in U.S. Pat. No. 5,131,998 (Jorgenson et al.), U.S. Pat. No. 5,389,221 (Jorgenson et al.), U.S. Pat. No. 5,326,445 (Lauer et al.), and U.S. Pat. No. 5,302,264 (Welch et al.). These disclosures of systems and methods are incorporated by reference herein.

In general, in the CE used in the present invention, a microcolumn (typically a fused silica capillary with a polyimide coating) filled with a buffer solution is used to separate the analytes in a sample. The two ends of the microcolumn (i.e., the capillary) are immersed in two separate volumes of the buffer. After introducing a sample at the inlet end of the microcolumn, A DC voltage (generally about 30 kV) is applied across the two ends of the microcolumn to draw the buffer through the microcolumn. Because of the electrical potential in the microcolumn, the analytes in a sample introduced in the inlet end of the microcolumn can be separated, depending on their charge densities, as they traverse through the microcolumn.

Generally, the inside diameter (i.d.) of the CE microcolumn is 5 µm to about 200 µm. The thickness of the column is such that the column will have the mechanical integrity and strength for operation under the pressure and appropriate for manipulation for capillary electrophoresis. The selection of the dimensions (including length, i.d., o.d.) and the voltage for the capillary electrophoresis operation for the separation of particular types of analytes (e.g., nucleic acids) in a sample is well known in the art.

Although a capillary electrophoresis (CE) system (such as CZE) is preferred, other columnar separation systems, such as electrochromatograph, liquid chromatograph, and the like, can be used as the second microcolumnar separation means, as long as the separation technique of first fluid conducting means is adequately orthogonal to that of the second microcolumnar separation means. Further, the flow-gating interface can be used to feed a sample fluid from a first fluid conducting means to a mass spectrometer (MS) for analysis. In this case, the MS is the separation (or analysis) technique. A microcolumnar section (i.e., the second microcolumnar section) of the flow gating interface can be considered the microcolumn of the second microcolumnar separation means.

Flow Gating Interface

The present flow gating interface couples the fluid flow between the first fluid conducting means to the second fluid conducting means (preferably between two microcolumns from two microcolumnar means). For example, to achieve two-dimensional separation (e.g., by LC and CE) of analytes in a sample, a liquid effluent from the microcolumn of the first fluid conducting means (e.g., LC) is further passed through the microcolumn of the second fluid conducting means (e.g., CE) to separate the analytes in the sample. To enable the control of such transfer of fluid between the two fluid conducting means, a flow gating interface according to the present invention is used to couple the microcolumns of the first and second fluid conducting means.

Figure 3:
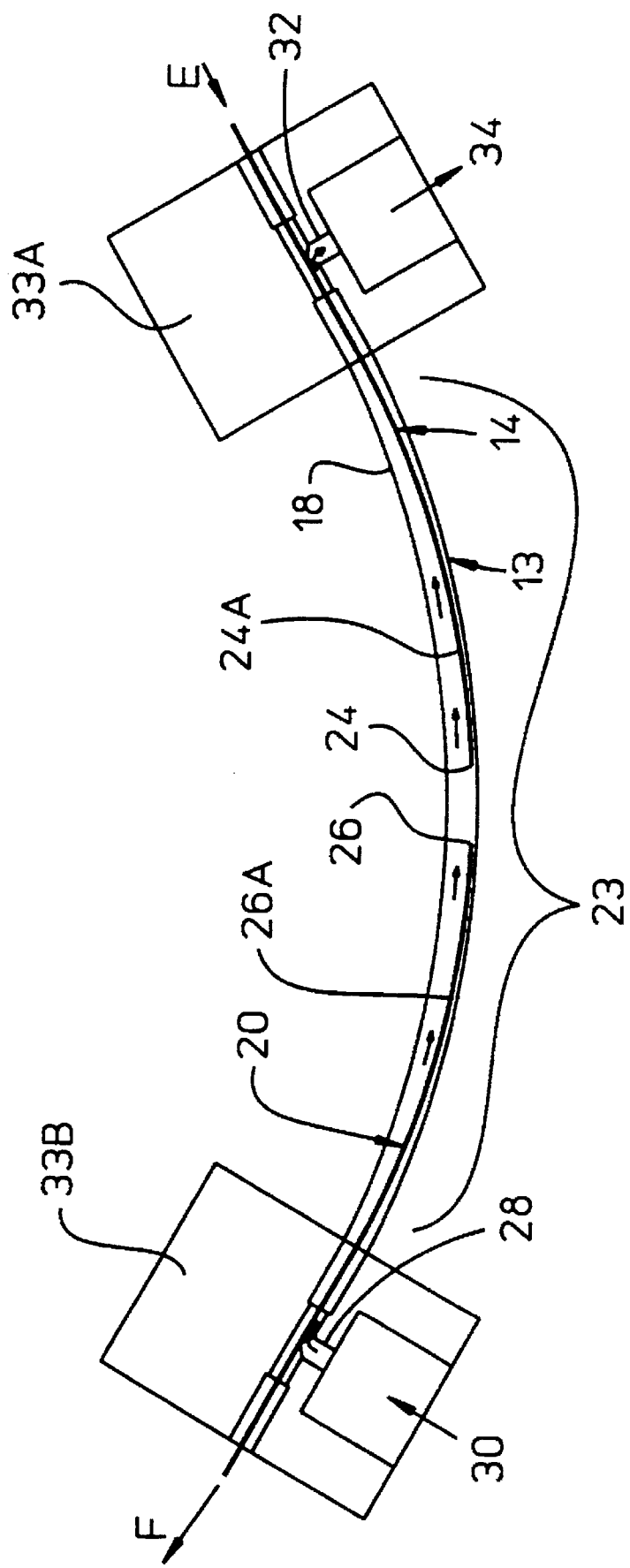
FIG. 3 shows a plan view of the flow gating interface in the microcolumnar analytical apparatus according to the present invention.

Referring to the embodiment of FIG. 3, the flow gating interface according to the present invention has a channel 13 for conducting a flush fluid flow in the channel (shown by arrows in the channel). A first microcolumnar section 14 having a lumen (not shown in FIG. 3, but shown as 16 in FIG. 4a) and an end portion 24A with an end 24 facing a second microcolumnar section 20 is disposed (i.e., enclosed or encircled) in the lumen 18 of the channel 13. Likewise, the second microcolumnar section 20 having a lumen (not shown in FIG. 3, but shown as 22 in FIG. 4) and an end portion 26A with an end 26 is disposed in the lumen 18 of channel 13. Because the microcolumnar sections 14, 20 are relatively small and long, they are somewhat flexible. However, the selected material of construction renders an elasticity to the microcolumn so that the microcolumn tends to return to its original shape when it is flexed. The channel 13 is bent so that it has a nonlinear (i.e., not straight) portion. In the embodiment shown in FIG. 3, the channel 13 is a tube having a generally circular across section.

Referring to FIGS. 4a, 4b, 5a and 5b the flexible nature of the microcolumnar sections enables these sections to flex without breaking. Thus, the curvature of the bent channel 13 causes the inwardly facing wall of the channel (lumenal wall) to press on the outside wall of the microcolumnar sections to constrain them from radial movement (i.e., in a direction perpendicular to the center line of the channel) at the points of contact. The center line for a tubular channel having a circular cross section is the tubular axis. In this way, the outlet end (or exit end) 24 of the first microcolumnar section 14 is proximate to the inlet end 26 of the second microcolumnar section 20. The distance between the outlet end 24 and the inlet end 26 is preferably small enough to prevent excessive loss of sample fluid (such as less than 20% loss) when sample fluid transfer is desired, yet large enough to keep fluid transfer low (such as below 10%) when transfer is not desired. For example, this distance (i.e., the gap) can be from about 0.2 to 0.5 the outside diameter of the smaller of the two microcolumnar sections.

In the embodiment shown in FIGS. 3, 4a, 4b, 5a and 5b the internal curvature of the circular cross section of the channel (lumenal wall) slidably confines interfacing ends 24 and 26 of the first and second microcolumnar sections 14, 20 respectively. As used herein, the term "interfacing end" refers to the end of a microcolumnar section that is proximate to the corresponding end of another microcolumnar section to which the microcolumnar section is coupled. The term "interfacing end portion" refers to the portion of a microcolumnar section including the interfacing end. The term "slidably confine" when referring to the end(s) or end portion(s) of the first and second microcolumnar sections in the channel means that the end(s) or end portion(s) are not rigidly affixed on the lumenal wall of the channel but slide thereon when the corresponding microcolumnar section(s) are moved in a direction generally parallel to (or along) the center line of the channel. The interfacing portions of the first and the second microcolumnar sections are aligned, i.e., their center lines are generally collinear and the ends 24, 26 are proximate to each other. As used in herein, the term "collinear" when referring to interfacing end portions of microcolumnar sections means the extrapolation of the center line of the interfacing end portion of a microcolumnar section about coincides with the center line of interfacing end portion of another microcolumnar section. Because the end portions 24A, 26A of the microcolumns are not fixedly attached to (i.e., detachable from) the channel and because the cross section of the channel has an arcuate (e.g., round) or angled (e.g. polygonal) perimeter, the inwardly facing wall on which the end portions rest is not flat. Thus, the channel continues to keep the end portions 24A, 26A in alignment even when they are moved.

Preferably, the first microcolumnar section 14 and the second microcolumnar section 20 have about the same inside diameter and outside diameter so that when ends 24 and 26 are proximate to each other they rest against the lumenal wall of the channel 13 and the lumenal openings face each other. This facilitates the transfer of fluid from the first microcolumnar section 14 to the second microcolumnar section 20.

Referring again to FIG. 3, the channel 13 is connected to a reservoir 30 of a flush fluid, which is an electricity conducting buffer when the second microcolumnar section is connected to an electrophoresis system. This connection can be by means of a fluid-conducting piece 28 (e.g., a T-shaped piece as shown in FIG. 3) through which the microcolumn section 20 extends. At the outlet end of channel 13 (i.e., proximate the first microcolumnar separation means), channel 13 is connected by means of another fluid-conducting piece 32 (e.g., a T-shaped piece as shown in FIG. 3) to another reservoir 34 which receives the fluid flushed out of the channel 13. Arrow E shows the direction of fluid flow from the first microcolumnar separation means to the first microcolumnar section. Arrow F shows the direction of flow of fluid from the second microcolumnar section to the second microcolumnar separation means. The channel 13 is secured to supports 33A, 33B to prevent movement of the channel.

It is to be understood that means other than T-shaped fluid conducting pieces can be used for connecting the channel to the reservoirs. For example, the channel 13 can be directly connected to a reservoir and the microcolumnar section extending through the wall of the channel. The elasticity of the channel, especially one made with polymeric material, can adequately seal around the microcolumnar section to prevent excessive leaking. Also, a reservoir may not even be need. For example, the channel can be arranged so that it is curved downward and contains the flush liquid by gravity such that the flush fluid can enter and exit by gravity.

For a capillary electrophoresis system, one electrode can be a fitting that is connected to the channel 13. For example, in FIG. 3, the T-shaped piece 28 can be made of a suitable metal to provide one electrode (e.g., ground potential). Because the flush fluid (liquid) conducts electricity, by providing another electrode connected to the outlet end of the capillary electrophoresis system, a suitable DC voltage can be applied across the two ends of the capillary electrophoresis capillary.

Referring to FIGS. 4a and 4b, the outlet end 24 of the first microcolumnar section 14 is positioned a short distance away from the inlet end 26 of the second microcolumnar section so that a gap 36 is formed therebetween. When it is not desired to transfer the fluid exiting the first microcolumnar section to the second microcolumnar section, the flushed liquid flow in the channel 13 is maintained so that the flush fluid passes across the gap 36 between end 24 and 26 to wash any liquid exiting the first microcolumnar section 14 downstream. When it is desired to transfer fluid exiting the first microcolumnar section to the second microcolumnar section, as shown in the embodiment of FIG. 4b, the flush fluid flow in the channel 13 is temporarily (i.e., reversibly) stopped. In this way, the flush fluid flow no longer passes across the gap 36. As a stream of liquid is continuously driven by the first microcolumnar separation means to exit the first microcolumnar section and liquid is continuously withdrawn into the second microcolumnar separation means by electromigration, fluid is transferred from the outlet ends 24 of the first microcolumnar section into the inlet end 26 of the second microcolumnar section.

Referring now to FIG. 5a, which shows another embodiment of the present invention, the flow gating interface of the present invention preferably has a means for moving at least one of the microcolumnar sections interfacing end portions 24A, 26A slidably in the channel. In the embodiment shown in FIG. 5, the first microcolumnar section, which is connected to the first microcolumnar separation means, can be slidably moved in a path about parallel to the center line of the channel 13 at the point where the outlet end 24 contacts the channel. Because the outlet end 24 of the first microcolumnar section 14 is constrained by the inwardly facing wall of the bent channel 13, as the microcolumnar section 14 is withdrawn backward (away from the second microcolumnar section) or pushed forward in the lumen of the channel 13, the end 24 of the first microcolumnar section is caused to slide on the inwardly facing wall of the channel 13. Arrowed mark G shows the directions of movement. When it is not desired to transfer fluid exiting the first microcolumnar section to the second microcolumnar section 20, the first microcolumnar section 14 is withdrawn a short distance to form a gap 38 between the ends 24 and 26 so that the flush fluid flow passing through the gap in channel 13 is adequate to prevent fluid exiting end 24 from entering end 26.

Referring now to FIG. 5b, to transfer fluid from the first microcolumnar section 14 to the second microcolumnar section 20, the first microcolumnar section is moved forward in the lumen of channel 13 so that end 24 of the first microcolumnar section 14 substantially abuts end 26 of the second microcolumnar section 20. In this fashion, even if the flush fluid flow in channel 13 is maintained, the proximity of end 24 and 26 to each other in a substantially parallel configuration enables efficient transfer of fluid from the first microcolumnar section 14 to the second microcolumnar section 20. It is allowable, but not necessary, that the ends 24, 26 touch each other, as long as they are adequately near and the velocities of fluid flow in the microcolumnar sections 24, 26 are adequately fast to prevent an excessive amount of fluid exiting the first microcolumnar section 24 from being flushed away. If desired, to further ensure that the fluid exiting the first microcolumnar section 14 would not be flushed downstream by the flush fluid flow, during the fluid transfer mode (i.e., when fluid transfer from first microcolumnar section to the second microcolumnar section is desired), the flush fluid flow can be temporarily and reversibly stopped as the embodiment of FIG. 4b.

Figure 6:
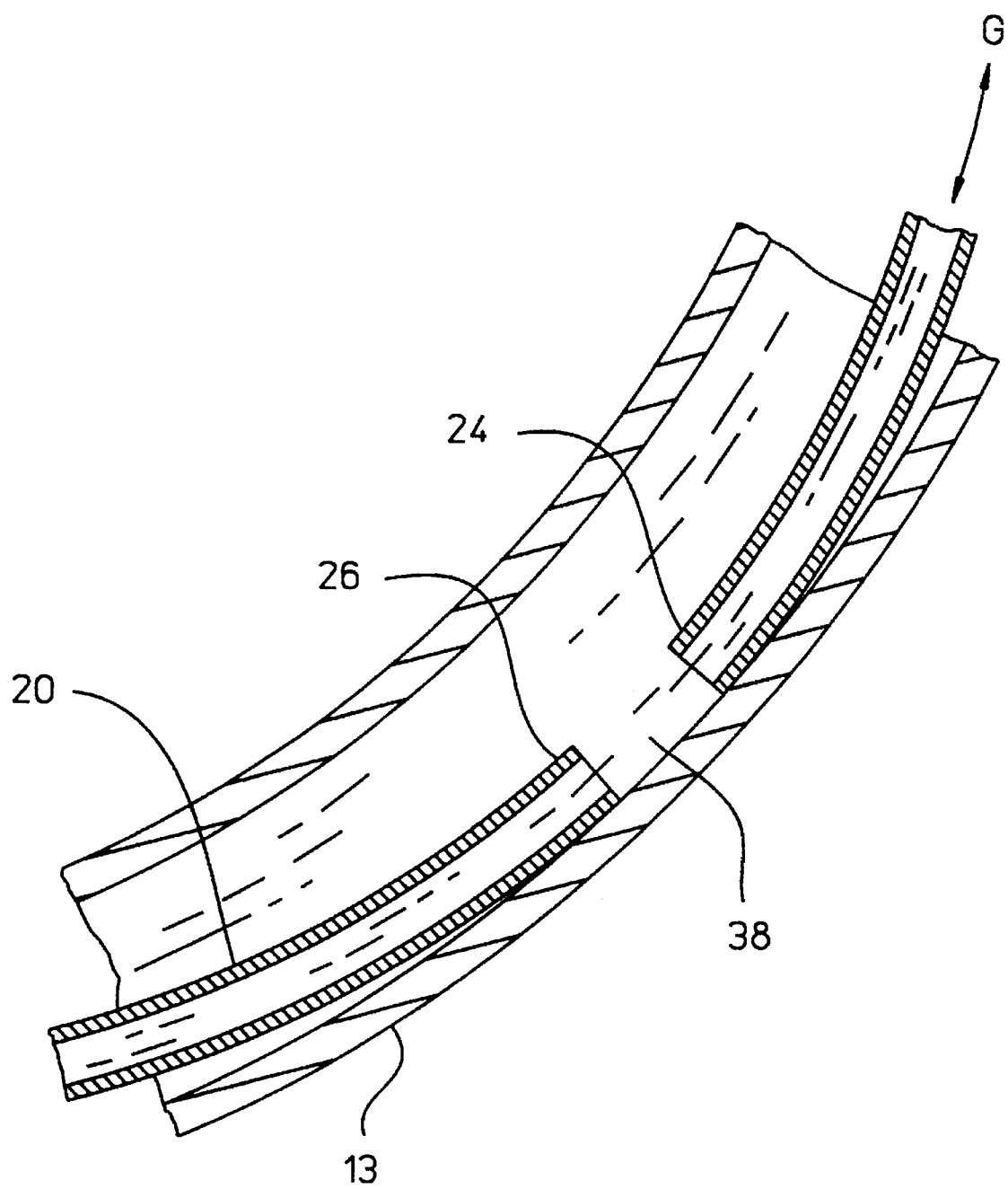

Preferably, although not necessarily, the channel 13 is made of a substance that has a smooth inwardly facing wall so that the ends 24, 26 can slide thereon repeatedly for an extended period of time without damage to the microcolumnar sections. Further, because of the orientation of the first microcolumnar section 14 and the second microcolumnar section 20 are preferably substantially parallel to the channel 13 (as shown in FIG. 6), a significant portion of the external surface of the first microcolumnar section 14 and the second microcolumnar section 20 can be made to contact the inwardly facing wall of the channel 13. In this way, damage to the ends 24 and 26 of the microcolumnar sections can be further reduced. Although it is preferred that the first microcolumnar section 14 and the second microcolumnar section 20 be arranged that when the two sections are brought together the ends 24 and 26 just abut, the flexibility of the microcolumnar sections allows a margin of error (e.g., about the outside diameter of either of the microcolumn sections, which in the case of a liquid chromatograph microcolumnar section can be about 150 µm to about 500 µm). Therefore, if in moving toward the second microcolumnar section the end 24 is pushed against the end 26, the microcolumnar sections 14, 20 can flex and absorb the shock of impact without damaging either microcolumnar section or moving them out of alignment.

Figure 7:
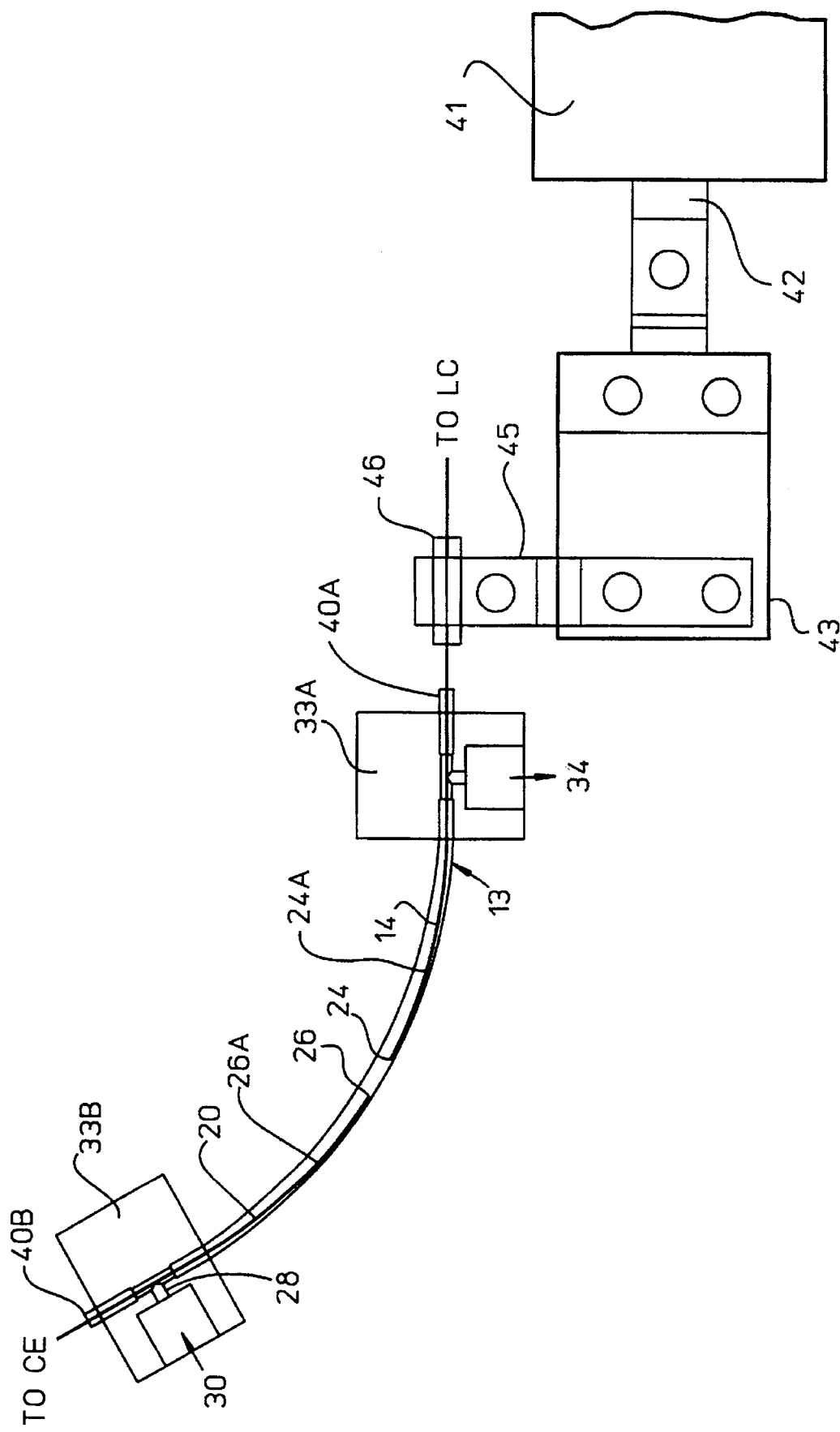
FIG. 7 is a plan view of a portion of the flow gating interface of the present invention, showing a mechanism for reciprocatively moving a microcolumnar section.

One or both of the microcolumnar sections 14, 20 can be moved reciprocatively along a path parallel to the center line of the channel 13 to reversibly decrease and increase the size of the gap 38, thereby controlling the transfer of fluid from the first and second microcolumnar sections. In the embodiment shown in FIG. 7, the outlet end of the channel 13 is connected by means of a T-shaped piece to a seal 40A (such as made of PTFE, e.g., TEFLON) through which the first microcolumnar section 14 (i.e., connected to the liquid chromatograph column) sealably and slidably extends. Similarly, a seal 40B seals the second microcolumnar section 20 connected to the CE system. A portion of the microcolumnar section of the first microcolumn separation means extending through the seal 40A is operatively secured to a solenoid means 41 for reciprocatively moving the microcolumnar section 14. The solenoid means 41 has a plunger 42 which is connected to a ball slide 43. The ball slide 43 in turn is connected to a gripper 45 which holds the microcolumnar section 14 protected by a protective TEFLON sleeve 46. Activating the solenoid means moves the plunger 42, which in turn moves the ball slide 43, the gripper 45, and subsequently the microcolumn section 14. The orientation and position of the solenoid means and the connecting mechanism to the microcolumnar section 14 are such that the activation of the solenoid means moves the microcolumnar section 14 slidably along the sleeve 40A. This results in the end portion 24A of the microcolumnar section 14 moving in a path parallel to the center line of the channel 13 at a point proximate the interfacing ends 24, 26. Mechanisms, other than solenoid means, can also be used for moving the microcolumnar sections. Such mechanism include, but are not limited to piezoelectric devices, devices using electric motors, and pneumatic devices. In the embodiment of FIG. 7, as an illustration, the microcolumnar section 14 is gripped and moved by the solenoid means and the associated mechanism. It is to be understood that the LC microcolumn, the CE microcolumn, or the other microcolumnar section can be moved in a similar manner.

Although, because of its simplicity of construction, a continuous, arcuate tube is preferred for the bent portion of the channel 13, channels of other shapes can also be used as long as they can be made in such a way to assist the first microcolumnar section and the second microcolumnar sections to align with each other in a substantially parallel fashion. A straight channel can also be used as long as the interfacing ends of the microcolumnar sections can be aligned proximate to each other.

Figure 8:
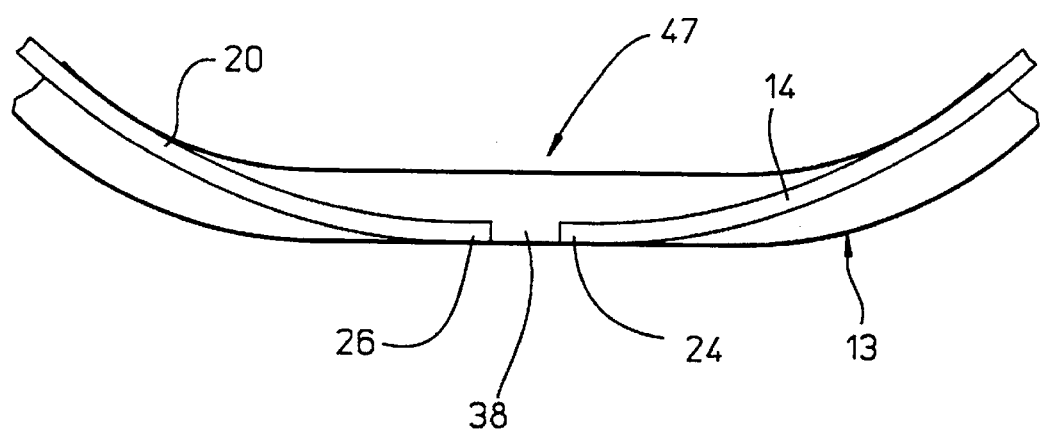
FIG. 8 is a plan view of a portion of another embodiment of the flow gating interface according to the present invention.

FIG. 8 shows another embodiment of the channel 13. In this embodiment, the interfacing portion 47 of the channel 13 (i.e., the mid portion of the channel which encloses the interfacing end portions 24A, 26A of the microcolumnar sections 14 and 22) is configured so that it is substantially straight. The straight portion of the bent channel 13 enables a longer portion on each of the microcolumnar sections 14, 20 proximate to the ends 24, 26 to contact the inwardly facing wall of the channel. This configuration has the advantage of allowing the interfacing end portions 24A, 26A of the microcolumnar sections to align with each other in a substantially straight fashion. Furthermore, the increase in area of contact between the reciprocatively movable microcolumnar section and the inwardly facing wall of the channel 13 can further reduce damage due to friction in sliding motion.

Figure 9:
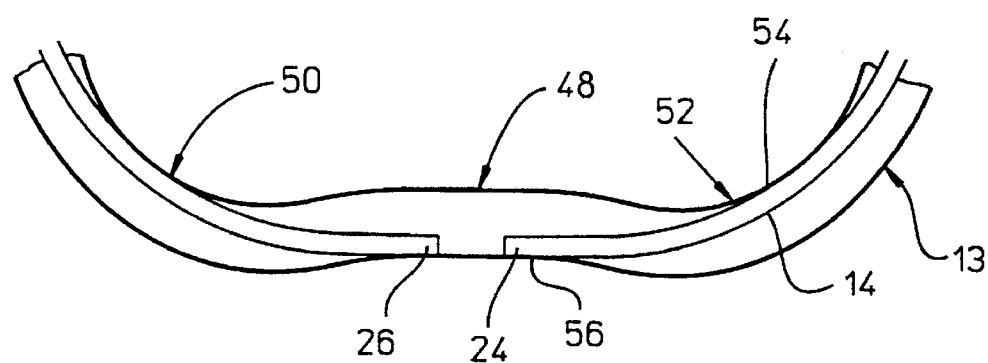
FIG. 9 is a plan view of a portion of yet another embodiment of the flow gating interface of the present invention.

The channel can have more than one bend. In the embodiment shown in FIG. 9, the channel 13 has a wavy configuration (i.e., having peak and valley, each of which can be considered one bend). The interfacing portion of the channel 13 has a peak 48 directed in the opposite direction to the valleys 50, 52. In this manner, the interfacing portion of the first microcolumnar section 14 contacts the inwardly facing wall of the channel 13 on surfaces 54, 56 on opposite sides of the center line of the first microcolumnar section 14 proximate the end 24. The shape of the wave in bent channel 13 is configured such that the interfacing end portions 24A, 26A of the first and second microcolumnar sections are substantially parallel.

Figure 10:
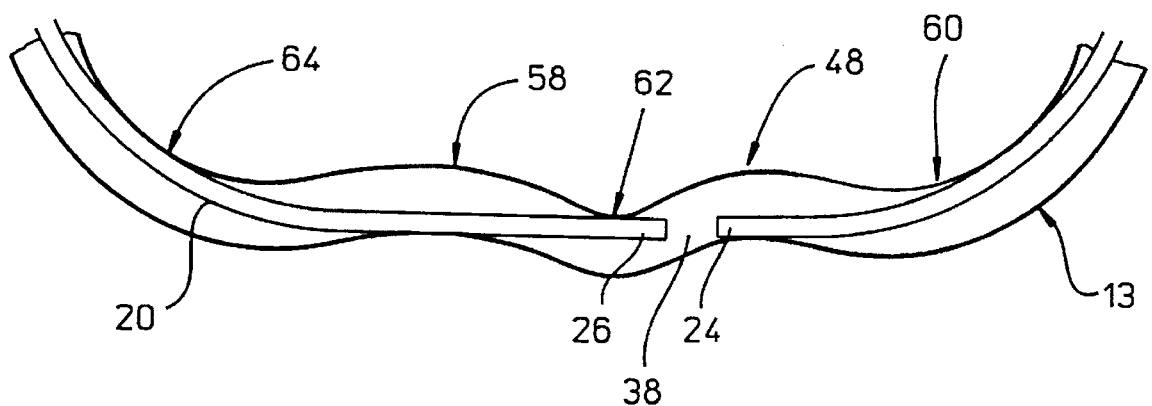
FIG. 10 is a plan view of a portion of yet another embodiment of the flow gating interface according to the present invention.

Other embodiments of the flow gating interface can be made to have more than three bends. In this way, at least one of the microcolumnar sections can be contacted and confined at three or more different points on the external surface thereof. FIG. 10 shows another embodiment in which the flow gating interface has a bent channel having a wavy configuration. In the embodiment, the channel 13 has two peaks 48, 58 and three valleys 60, 62, 64. The second microcolumnar section 20 is contacted and confined by the inwardly facing wall of the channel 13 proximate valleys 62, 64 and peak 58 on surfaces on opposite sides of the center line of the second microcolumnar section. The shape and dimensions of the channel, depending on the outside diameter of the second microcolumnar section 20, can be selected such that the interfacing end portion 26A of the second microcolumnar section proximate the gap 38 is aligned with the interfacing end portion 24A of the first microcolumnar section.

Because the respective interfacing end portions 24A, 26A of the first and the second microcolumnar section rest on different peaks of the bent channel, microcolumnar sections of different outside diameters can be used and still be aligned to be collinear. By having more than two points of the channel 13 contacting and confining the second microcolumnar section, the second microcolumnar section can be slidably moved in a path substantially parallel (even absolutely parallel if preferred) to the center line of the channel. This ensures that the ends 24, 26 are adequately aligned and abut each other when transfer of fluid from the first microcolumnar section 14 to the second microcolumnar section 20 is desired. However, if desired, the microcolumnar interfacing end portions 24A, 26A can be aligned to be collinear with each other but form an angle with the center line of channel (as in FIG. 10). Preferably, the angle is less than about 45° because of the ease of construction. In such a configuration, the flow of flush fluid and the fluid in the microcolumnar section can be considered to be "generally parallel" herein. The configuration of FIGS. 7, 8, 9 can also be used in a flow gating interface wherein the microcolumnar sections are stationary (i.e., neither of which is moved during operation), for example, by controlling the flush fluid flow in a manner shown in FIGS. 4a and 4b.

Figure 11:
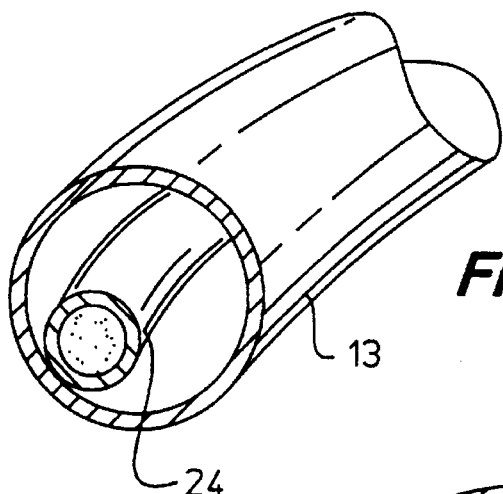
FIG. 11 shows an isometric view of an embodiment of the flow gating interface having a channel with a circular cross section at the interfacing end of a microcolumnar section.
Figure 12:
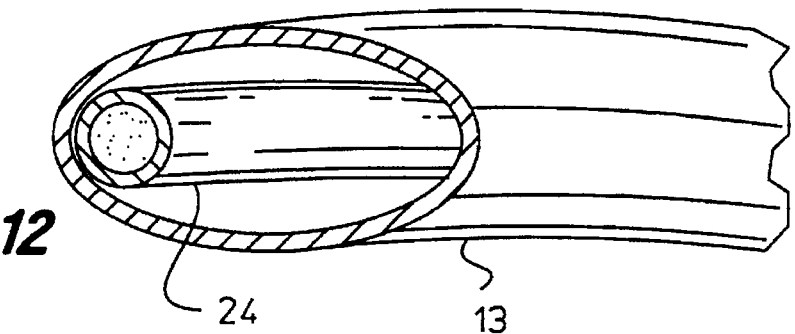
FIG. 12 shows an isometric view of an embodiment of the flow gating interface having a channel with an oval cross section at the interfacing end of a microcolumnar section.
Figure 13:
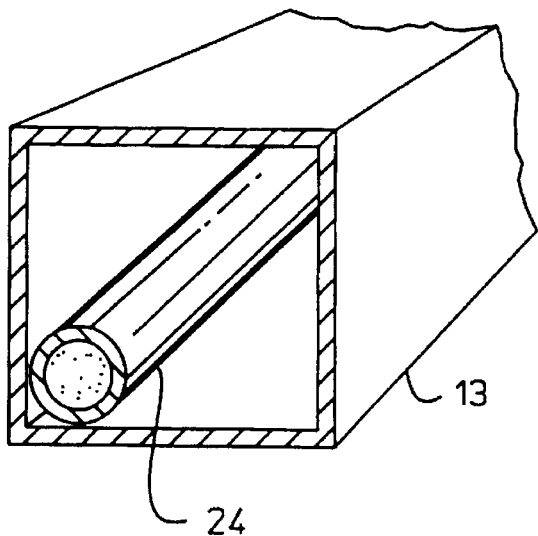
FIG. 13 shows an isometric view of an embodiment of the flow gating interface having a channel with a square cross section at the interfacing end of a microcolumnar section.
Figure 14:
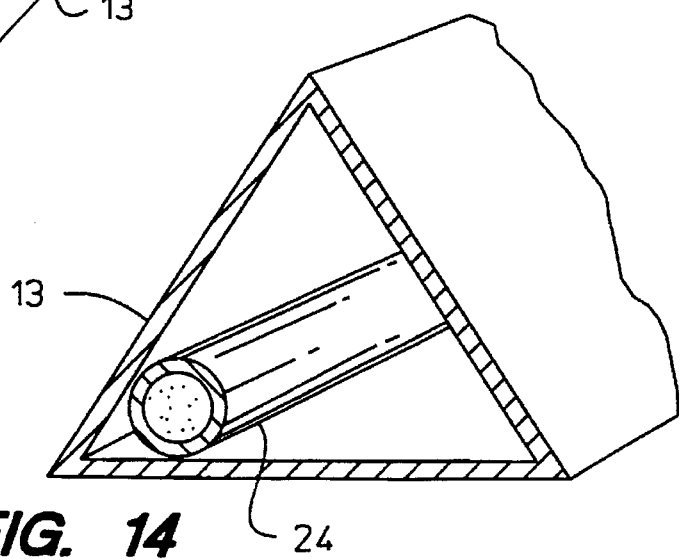
FIG. 14 shows an isometric view of an embodiment of the flow gating interface having a channel with a triangular cross section at the interfacing end of a microcolumnar section.

A preferred embodiment of the flow gating interface having a tubular channel with a circular cross-section (as shown in FIG. 11) has been described. However, channels having various cross-sectional shapes can be also used: for example, oval cross-section (FIG. 12), square cross-section (FIG. 13), triangular cross-section (FIG. 14), rectangular cross-section, other polygonal cross-section, and the like. In channels with flat inwardly facing walls, two adjacent walls connect to form the groove for guiding the position of the microcolumnar interfacing end sections.

The channel can be made with relatively rigid material that enables the channel to maintain a bent shape. Suitable materials include, but are not limited to, metal such as stainless steel, copper, transparent material such as glass, polymer such as polytetrafluoroethylene, polyethylene, and the like. One factor for the selection of material of construction for the channel is chemical compatibility with the flush liquid and the samples. Preferably the channel is transparent, or translucent, so that the position of the interfacing ends of the microcolumnar sections can be determined from outside the channel. However, even if the channel is made of a nontransparent or translucent material, because the channel can be constructed to have relatively thin wall of an appropriate material, the position of the microcolumnar interfacing ends may be determined by techniques such as ultrasound and X-ray imaging. Such imaging is facilitated by the orientation of the channel and the microcolumnar sections. In general, the channel and the interfacing end portions of the microcolumnar sections can be arranged such that, at a location proximate to the ends of the end portions, at least one line can be found to be about perpendicular to the center line of the channel and the end portions. In other words, the end portions lie on the plane of the curvature of the bend at the interfacing region.

The dimensions of tile channel are selected to suit the need for the application, including, for example, the flexibility, material of construction, and dimensions of the microcolumnar sections, as well as the flow rates of the sample fluid and the flush fluid. Generally, for convenience of construction, the channel is tubular and the ratio of the i.d. of the channel to the o.d. of the microcolumnar section is, but not necessarily, from about 1.2 to 10. In fact, the channel can be a trough. In some cases, the channel can be a container much larger than the microcolumnar section. The end portions of the microcolumnar sections can rest against a wall of the channel and an agitating means, such as a stirrer, can be used to move fluid through the gap between the ends of the microcolumnar sections.

The microcolumnar sections can be the microcolumns from the first and the second microcolumnar separation means or they can be discrete sections connected to the microcolumns by a coupling sleeve or fitting (which can be a polymeric material, such as the TEFLON sleeve tubing disclosed in U.S. Pat. No. 5,389,221). Preferably, in the case of CE, the microcolumnar section is part of the microcolumn (i.e., capillary) of the CE system. In the case of LC, because the LC microcolumn is typically larger than the CE microcolumn, preferably, the LC microcolumn is coupled to a microcolumnar section having the same i.d. and o.d. as the CE microcolumnar section.

Operation of the Apparatus

Generally, the first microcolumnar separation means is operated under standard procedures to elute the analytes. As the fluid exits the first microcolumnar section, it is sampled and analyzed by the second microcolumnar separation means. Each of such samples is eluted through the second microcolumnar separation means. Generally, a higher rate of sampling allows better separation of the analytes because the eluted "peaks" in the first microcolumnar separation means will not be lumped together in the second fluid conducting means. When transfer of fluid between the microcolumnar section is not desired (e.g., between sampling steps to obtain more data points), the flush fluid is allowed to pass through the gap between the interfacing ends of the microcolumnar sections. In this way, the fluid exiting the outlet end of the first microcolumnar section is substantially prevented from entering the second microcolumnar section. As previously described to allow sampling, the flush fluid flow can be temporarily stopped and/or one or both of the microcolumnar sections can be moved to substantially abut the interfacing ends thereof. In this way, for sampling, one can substantially reduce the proportion of the fluid (which exits the first microcolumnar section) that is carried away by the flush fluid. After a sample has been transferred to the second microcolumnar interfacing end, the flush fluid flow can be resumed and/or the microcolumnar interfacing ends returned to their position prior to sampling. The following example illustrates the operation of the apparatus of the present invention.

EXAMPLE

In this example, the first microcolumn is a flexible fused silica capillary with a polyimide coating outside (Polymicro Technologies, Phoenix, Ariz.). It has a 0.025 mm i.d., a 0.365 mm o.d., and a length adequate to link the LC separation column to the interface apparatus. The length is about 50 cm (but may be as little as 5 cm or even nonexistent if the LC separation takes place in the first microcolumn). The end of the first microcolumn extends about 3 cm into a glass tube which has an i.d. of about 1.25 mm and an o.d. of about 1.65 mm and is about 7 cm long. The glass tube is rigid and has the approximate shape shown in FIG. 9. The second microcolumn is a capillary electrophoresis column. It is also fused silica with a polyimide coating, and has an o.d. of 0.365 mm and an i.d. of 0.013 mm. The inlet end of the second microcolumn extends about 3 cm into the other end of the glass tube, resting end-to-end with the first microcolumn, and separated by a gap of a few microns (but may be up to 10 mm, depending on the specific configuration).

At each end of the glass tube is a T-fitting which holds the glass tube firmly and has a port for the flush buffer (fluid) and a port for the capillary, which runs straight through the fitting into the glass tube. The fitting allows the flush buffer to flow through the glass tube, around and between the capillaries, and out through the other fitting. The flush buffer flow rate is between 0.2 ml/min and 5 ml/min. One fitting is made of PEEK and the other is stainless steel. Near the exit end of the CE column (or capillary) is a detector and the end of the CE capillary is immersed in a reservoir containing buffer. There is an electrical connection to the flushing buffer in the glass tube, made by grounding the stainless steel fitting, and an electrical connection at the other end of the CE capillary, made by a platinum electrode in the buffer reservoir which is connected to a high voltage power supply (Spellman High Voltage Electronics, Plainview, N.Y.).

When the system is in operation, effluent flows out of the first microcolumn and is selectively transferred into the CE capillary. In the stop-flush configuration, the gap between the two microcolumns is small, from 1–500 microns (μm). Most of the time there is high voltage (typically 500 V/cm) across the CE capillary, and there is flush buffer flowing through the glass tube to wash away the effluent from the first microcolumn and provide a reservoir for electroosmotic flow through the CE capillary. The flush buffer enters the fitting at the CE capillary, and exits the fitting at the first microcolumn, thus the flow is against the direction of the first microcolumn effluent flow. Intermittently, the flush buffer flow is stopped by switching a valve, and the voltage across the CE capillary may be changed somewhat, perhaps to 200 V/cm. At this time, the effluent is no longer washed away and is drawn into the CE capillary electrophoretically, if the molecules are charged appropriately, or hydrodynamically by the electroosmotic flow. When the flush buffer is switched on again the effluent is again washed away and an injection of the effluent has been made into the CE capillary. Typical timing for this switching is about 30–60 seconds of flushing and 1–3 seconds of stopped-flush.

In the sliding capillary configuration, most of the time the gap between the microcolumns is from 1–5 mm, the voltage across the CE capillary is around 500 V/cm, and the flush buffer is flowing through the glass tube as above. Intermittently, the capillaries are forced together by sliding the first microcolumn using a solenoid such that their gap approaches zero, and effluent from the first microcolumn is drawn into the CE capillary either electrophoretically or electroosmotically, as above. The fitting around the first microcolumn is loose enough to allow sliding yet tight enough to provide a seal to prevent the flush buffer from leaking out. The gap between the capillaries is held at zero for a time of about 0.05 seconds to 3 seconds, and this is done with a period of about 10–60 seconds. When the capillary gap is restored, the flush buffer resumes washing away the first microcolumn effluent, and an injection has been made into the CE. The voltage across the CE microcolumn need not but may be changed for the injection.

The flush buffer used was 10 mm phosphate ($Na_2HP0_4.H_2O$, Mallinckrodt, Paris, K.Y.) with triethylamine (TEA) (Aldrich, Milwaukee, Wis.) added to pH 11.5. The sample was tetramethyhlrhodamine-5-isothiocyanate (TRITC, Molecular Probes, Eugene, Ore.) derivitized CE peptide mix (Sigma Chemical Co., St. Louis, Mo.). The concentration of each derivitized peptide was approximately $1 \times 10^{-7}$M in 30:70 acetonitrile:HPLC grade water (Sigma) with 0.1% trifluoroacetic acid (TFA, Aldrich) in the acetonitrile and water. A sample volume of 0.01 ml was injected into the LC column (Hypersil ODS 2.1 mm×100 mm, 0.005 mm particles, Hewlett-Packard, Palo Alto, Calif.) on a Hewlett-Packard 1090 LC instrument. The LC method was an isocratic separation using 40% acetonitrile and 60% HPLC grade water, also containing 0.1% TFA, run for 35 minutes at a flow rate of 0.2 ml/min.

Figure 15:
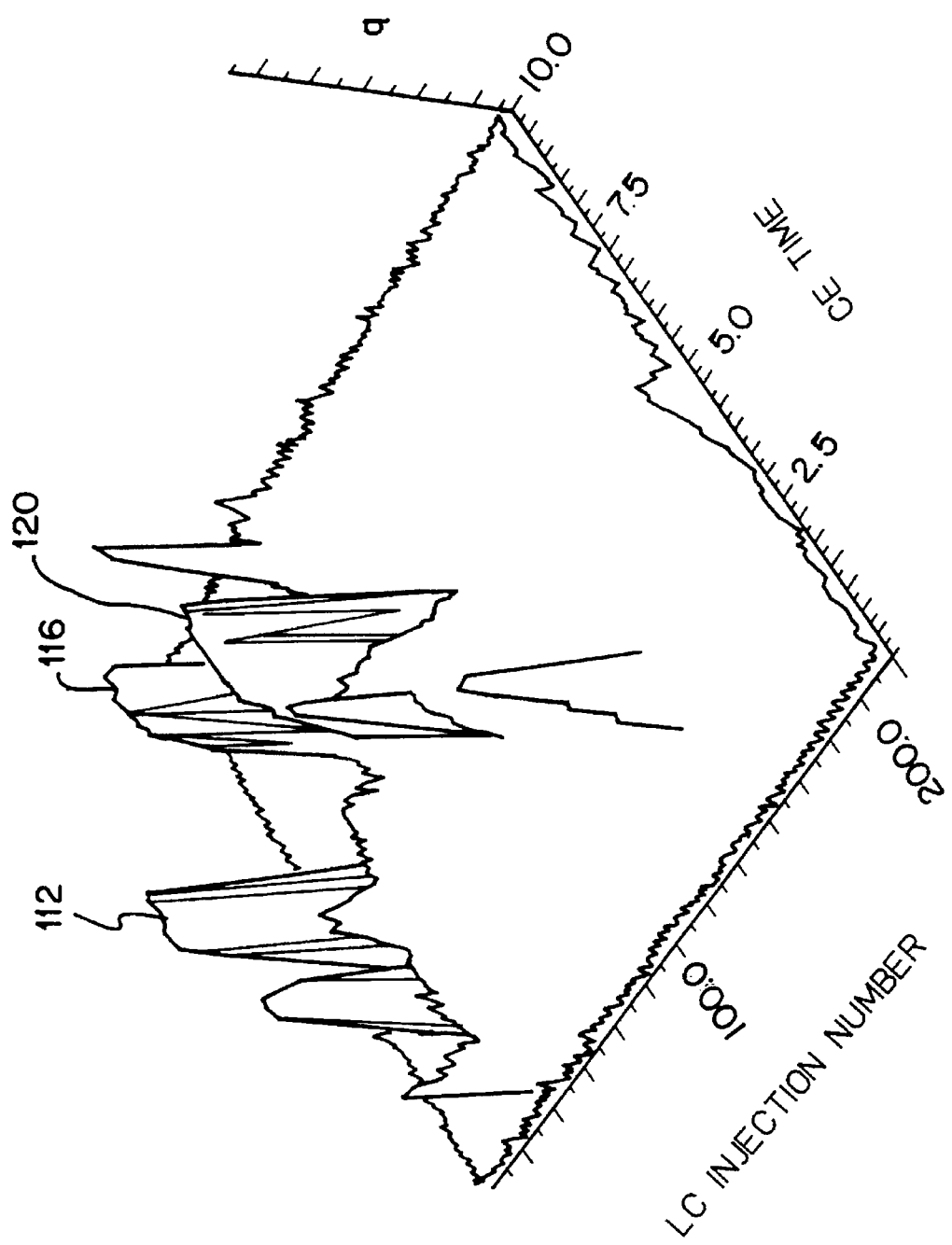
FIG. 15 is a graphical representation of the result of the separation of analytes in a sample using an analytical apparatus having LC and CE interfaced according to the present invention.

The effluent from the LC column was split so that only about 10% entered the first microcolumn extending to the interface. The gap between the two microcolumns was about 3 mm, and was closed to make the microcolumns contact and allow injection for 1 second every 10 seconds. The flush buffer flow was constant at a rate of about 5 ml/min. The voltage at the CE inlet was ground, and was −10 kV at the outlet of the 26 cm long capillary. The CE capillary had an i.d. of 0.013 mm, and an o.d. of 0.365 mm. Detection was made at 19 cm from the CE inlet using a laser induced fluorescent system, composed of a 1.5 mW green (543.5 nm) Helium-Neon laser (Melles Griot, Irvine, Calif.) which excites the TRITC to fluoresce around 577 nm. A photomultiplier tube (Hamamatsu U.S.A., Bridgewater, N.J.) was used to detect the fluorescence signal. FIG. 15 gives the results using the sliding capillary configuration coupling an LC separation to a CE separation. The results are displayed in a three dimensional (3D) form representing the CE separation time dimension on the x-axis, the LC separation time dimension on the y-axis, and the fluorescence signal on the z-axis. The figure shows sample constituents separated by the LC separation mechanism (reverse phase, or hydrophobicity-based) on the y-axis ("LC Injection Number" axis) and by the CE separation mechanism (charged-based) on the x-axis (or "CE Time" axis). The axis q (with arbitrary unit) shows the concentrations (i.e., quantities) of analytes. The height of a peak represents the concentration of an analyte. However, the tallest peaks are truncated (thus showing cut tops) for clarity. For example, peaks 112, 116, 120, etc. represent different constituents (or analytes) separated by the apparatus. This apparatus allows regular and numerous sampling of the LC effluent for CE analysis, permitting separation of more sample constituents than would be the case using one mechanism (LC or CE) alone.

Although the illustrative embodiments of the analysis system of the present invention and the method of using the system have been described in detail, it is to be understood that the above-described embodiments can be modified by one skilled in the art, especially in sizes and shapes and combination of various described features without departing from the spirit and scope of the invention. For example, channels of different shapes can also be used. The channels can be bent to have smooth curves, smooth waves, angular bents, loops, and the like. Various combination of different microcolumnar separation techniques can be used for the first and second microcolumnar separation means. For example, CE can be used upstream and downstream of the flow gating interface. In this case, for example, a vacuum assisted CZE (similar to that disclosed U.S. Pat. No. 5,326,445) can be used in the downstream separation technique. Moreover, the flow gating interface of the present invention can be used in nonseparation applications, as in sampling the effluent with a microcolumn. In some conventional sampling systems, a sampling microcolumn is dipped in a body of the fluid to be sampled and then the microcolumn is lifted from the fluid and dipped in a buffer. In such conventional systems, surface tension causes a drop to form around the tip of the microcolumn and therefore results in less reliable control of the amount sampled than using the present invention. Using the present interface obviates such dipping processes. The flow gating interface of the present invention can also be used to obtain a make-up flow by diluting a first liquid stream with another stream (a diluent fluid). The flow of either the first fluid or the diluent fluid can be controlled by the present interface. The flush fluid in the channel can also be used for dilution as it and the effluent from the first microcolumnar section are drawn into the second microcolumnar section.

What is claimed is:

1. A microcolumnar analytical apparatus, comprising:
    a flow gating interface comprising:
    (A) a first microcolumnar section having a center line, an outlet end portion having an outlet end, and a lumen for conducting a fluid flow;
    (B) a second microcolumnar section having a center line, an inlet end portion having an inlet end, and a lumen for conducting a fluid flow; and
    (C) a channel having a center line and inwardly facing wall, the channel enclosing at least a portion of the first microcolumnar section and at least a portion of the second microcolumnar section for conducting a flush fluid flow past said ends of the microcolumnar sections, the inwardly facing wall of the channel nonfixedly constraining and aligning said end portions of the first and second microcolumnar sections due to the relative curvature and elasticity of the microcolumnar sections and the channel;
    a first fluid conducting means for transferring a fluid sample, the first fluid conducting means being operatively connected to and in fluid communication with the first microcolumnar section;
    a flush liquid supply means operatively connected to and in fluid communication with the channel for flowing the flush fluid through the channel; and
    a second fluid conducting means for analysis of an effluent fluid sample exiting the first microcolumnar section, the second fluid conducting means having a microcolumn and being operatively connected to and in fluid communication with the second microcolumnar section.

2. The analytical apparatus according to claim 1 wherein the outlet end of the first microcolumnar section is proximate the inlet end of the second microcolumnar section and oriented such that the center lines of the outlet end portion and the inlet end portion are generally parallel to facilitate the transfer of fluid from the outlet end of the first microcolumnar section to the inlet end of the second microcolumnar section when desired.

3. The analytical apparatus according to claim 1 wherein the channel and said end portions of the microcolumnar sections are arranged such that said center lines at a location proximate said ends of said end portions lie on a plane.

4. The analytical apparatus according to claim 1 wherein the channel has one or more arcuate portions such that the curvature of the one or more arcuate portions and the elasticity of the first and second microcolumnar sections cause the wall of the one or more arcuate portions to press on the microcolumnar sections to align the microcolumnar sections so that the center lines of said end portions and the channel are generally parallel.

5. The analytical apparatus according to claim 4 wherein the channel has three or more arcuate portions such that each of the microcolumnar sections is pressed by two adjacent but generally oppositely directing arcuate portions on the wall of each of the microcolumnar sections so that said ends of the first and second microcolumnar sections are proximate and the center lines of the sections at said ends are collinear.

6. The analytical apparatus according to claim 1 wherein the channel has an arcuate portion such that the curvature of the arcuate portion and the elasticity of the first and second microcolumnar sections cause said ends of the microcolumnar sections to rest against the wall of the channel such that the center lines of the microcolumnar sections at said ends are substantially collinear with each other but are offset from the center line of the channel.

7. The analytical apparatus according to claim 1 wherein said ends divide the flush fluid flow into an upstream portion and a downstream portion and the gating interface is adapted such that the outlet end of the first microcolumnar section is separated from the inlet end of the second microcolumnar section with a sufficient distance to form a gap such that when transfer of fluid from the first microcolumnar section to the second microcolumnar section is not desired the flush fluid flushes the fluid exiting the first microcolumnar section from the gap downstream to prevent said exiting fluid from entering the second microcolumnar section.

8. The analytical apparatus according to claim 7 wherein the microcolumnar sections have similar outside diameters and said gap between said ends of the microcolumnar sections is from 0.2 to 1 times the outside diameter of the microcolumnar sections for flushing.

9. The analytical apparatus according to claim 7 further comprising a control means for stopping the flush fluid flow in the channel when transfer of fluid from the first microcolumnar section to the second microcolumnar section is desired.

10. The analytical apparatus according to claim 7 further comprising a means for operatively moving at least one of the microcolumnar sections to decrease the distance between said ends of the microcolumnar sections to facilitate transfer of fluid from the first microcolumnar section to the second microcolumnar section when such transfer is desired and to increase the distance between said ends of the microcolumnar sections to prevent transfer of fluid form the first microcolumnar section to the second microcolumnar section when such transfer is not desired.

11. The analytical apparatus according to claim 10 wherein at least one of the outlet end of the first microcolumnar section and the inlet end of the second microcolumnar section moves in a path substantially parallel to the center line of the first microcolumnar section at said ends.

12. The analytical apparatus according to claim 10 wherein at least one of the outlet end of the first microcolumnar section and the inlet end of the second microcolumnar section moves in a path that is nonparallel to the center line of the channel at said ends of the microcolumnar sections.

13. The analytical apparatus according to claim 10 further comprising solenoid means for moving the at least one of the microcolumnar sections.

14. The analytical apparatus according to claim 1 wherein said first and second microcolumnar sections are slidably constrained by the channel.

15. The analytical apparatus according to claim 1 wherein the channel includes a section sufficiently transparent such that the positions of said ends can be observed therethrough.

16. The analytical apparatus according to claim 1 wherein the first fluid conducting means comprises an analytical microcolumn.

17. The analytical apparatus according to claim 16 wherein the first fluid conducting means has a chromatographic microcolumn and the second fluid conducting means has a capillary electrophoresis capillary.

18. A microcolumnar analytical apparatus having a flow gating interface system for interfacing a first microcolumn and a second microcolumn, comprising:
a flow gating interface comprising:
(A) a first microcolumnar section having a center line, an outlet end portion having an outlet end, and a lumen for conducting a fluid flow;
(B) a second microcolumnar section having a center line, an inlet end portion having an inlet end, and a lumen for conducting a fluid flow; end
(C) a channel having a center line and enclosing at least a portion of the first microcolumnar section and at least a portion of the second microcolumnar section for conducting a flush fluid flow past said ends of the microcolumnar sections, the inwardly facing wall of the channel slidably constraining said end portions of the first and second microcolumnar sections, due to the relative curvature and elasticity of the microcolumnar sections and the channel, such that the outlet end of the first microcolumnar section is proximate the inlet end of the second microcolumnar section and such that the center lines of the outlet end portion and the inlet end portion are generally parallel to facilitate the transfer of fluid from the outlet end of first microcolumnar section to the inlet end of the second microcolumnar section when desired;
a means for reciprocatively, operatively moving at least one of the microcolumnar sections to alternatively decrease and increase the distance between said ends of the microcolumnar sections;
a first microcolumnar means for analysis of a fluid sample, the first microcolumnar means having a microcolumn operatively connected to and in fluid communication with the first microcolumnar section;
a flush liquid supply means operatively connected to and in fluid communication with the channel for flowing the flush fluid through the channel; and
a second microcolumnar means for analysis of an effluent fluid sample from the first microcolumnar section, the second microcolumnar means having a microcolumn operatively connected to and in fluid communication with the second microcolumnar section.

19. A microcolumnar analytical apparatus having a flow gating interface system for interfacing a first microcolumn and a second microcolumn, comprising:
a flow gating interface comprising:
(A) a first microcolumnar section having a center line, an outlet end portion having an outlet end, and an tureen for conducting a fluid flow;
(B) a second microcolumnar section having a center line, an inlet end portion having an inlet end, and a lumen for conducting a fluid flow; and
(C) a bent channel having a center line and enclosing at least a portion of the first microcolumnar section and at least a portion of the second microcolumnar section for conducting a flush fluid flow past said ends of the microcolumnar sections, the inwardly facing wall of the bent channel nonfixedly constraining said end portions of the first and second microcolumnar sections, due to the relative curvature and elasticity of the microcolumnar sections and the channel, such that the outlet end of the first microcolumnar section is proximate the inlet end of the second microcolumnar section and such that the center lines of the outlet end portion and the inlet end portion are generally parallel to facilitate the transfer of fluid from the outlet end of first microcolumnar section to the inlet end of the second microcolumnar section when desired;
a first microcolumnar means for analysis of a fluid sample, the first microcolumnar means having a microcolumn with an inlet end and an outlet end, the outlet end being operatively connected to and in fluid communication with the first microcolumnar section;
a flush liquid supply means operatively connected to and in fluid communication with the channel for flowing the flush fluid through the channel; and
a second microcolumnar means for analysis of an effluent fluid sample from the first microcolumnar section, the second microcolumnar having a microcolumn with an inlet end and an outlet end, the inlet end being operatively connected to and in fluid communication with the second microcolumnar section.

20. A method for analyzing a liquid sample, comprising:
(a) transferring the liquid sample through a first microcolumnar device which includes a first microcolumn;
(b) coupling the first microcolumn to a second microcolumn which is part of a second microcolumn device to control fluid flow from the first microcolumn to the second microcolumn, comprising:
(A) using the inwardly facing wall of a channel to nonfixedly constrain an outlet end portion of a first microcolumnar section operatively connected to and in fluid communication with the first microcolumn and to constrain an inlet end portion of a second microcolumnar section operatively connected to and in fluid communication with the second microcolumn, by the relative curvature and elasticity of the microcolumnar sections and the channel, such that an outlet end of said outlet end portion is proximate an inlet end of said inlet end portion and such that center lines of said outlet end portion are inlet end portion are substantially parallel to facilitate the transfer of fluid from said outlet end of the first microcolumnar section to said inlet end of the second microcolumnar section when desired, the channel being adapted to conduct a flush fluid flow;

(B) substantially preventing transfer of fluid from the first microcolumnar section to the second microcolumnar section by flushing the flush fluid in the channel through a gap between the outlet end of the first microcolumnar section and the inlet end of the second microcolumnar section to substantially carry away fluid exiting said outlet end; and (C) transferring fluid from the first microcolumnar section to the second microcolumnar section by reducing the amount of fluid exiting said outlet end from being carried away by the flush fluid; and (c) analyzing the fluid transferred from the first microcolumnar device to the second microcolumnar device.

21. The method according to claim 20 wherein the fluid is transferred from the first microcolumnar section to the second microcolumnar section by at least one of reversibly stopping the flush fluid flow in the channel and reversibly positioning said outlet end of the first microcolumnar section and said inlet end of the second microcolumnar section in a substantially abutting configuration by reversibly moving at least one of the microcolumnar sections to narrow the gap such that the amount of fluid exiting the outlet end being carried away by the flush fluid is reduced.

22. The method according to claim 20 wherein the step of using a channel to constrain comprises arranging the channel and said end portions of the microcolumnar sections such that said center lines at a location proximate said ends of said end portions lie on a plane.

23. The method according to claim 20 wherein the step of using a channel to constrain comprises using a bent tube having a circular cross section such that the bent tube aligns said end portions of the microcolumnar sections and such that the center line of the channel is generally parallel to that of said end portions.

24. The method according to claim 20 wherein the step of using a channel to constrain comprises using a channel with an arcuate portion and said end portions of the microcolumnar sections are arranged such that the curvature of the arcuate portion and the elasticity of the microcolumnar sections cause said ends of the microcolumnar sections to rest against the inwardly facing wall of the channel such that the center lines of the microcolumnar sections at said ends substantially collinear with each other but are offset from the center line of the channel.

25. The method according to claim 20 wherein the step of using a channel to constrain comprises using a bent channel having three or more arcuate portions and arranging said end portions of the microcolumnar sections such that each of the microcolumnar sections is pressed by two adjacent but generally oppositely directing arcuate portions on the wall of the each of the microcolumnar sections so that said ends of the first and second microcolumnar sections are proximate and the center lines of the microcolumnar sections at the ends are collinear.

26. The method according to claim 20 wherein the step of using a channel to constrain comprises using a channel having a section that is transparent and the method further comprising adjusting the position of said ends of the microcolumnar sections while visually evaluating the position of said ends through said transparent section prior to steps (B) and (C).

27. The method according to claim 20 wherein the step of using a channel to constrain comprises using a bent channel and the method further comprises moving one of the first and second microcolumnar sections by a solenoid moving means so that said moved section reciprocatively slides on the inwardly facing wall of the channel between a first position wherein said ends of the first and second microcolumnar sections are in substantially abutting configuration for transfer of fluid from the first microcolumnar section to the second microcolumnar section and a second position wherein a sufficient gap results between said ends for the flush fluid to pass therethrough to prevent the transfer of fluid from the first microcolumnar section to the second microcolumnar section.

28. A method of making an analytical apparatus for analyzing a liquid sample, comprising:

(a) providing a first fluid conducting means for transferring the fluid sample;

(b) providing a second fluid conducting means for analysis of the fluid sample, the second fluid conducting means having a microcolumn;

(c) coupling the first fluid conducting means to the microcolumn of the second fluid conducting means with a flow gating interface to control fluid flow from the first fluid conducting means to the microcolumn of the second fluid conducting means, the flow gating interface comprising:

(A) a first microcolumnar section having a center line, an outlet end portion having an outlet end, and lumen for conducting a fluid flow, the first microcolumnar section being operatively connected and in fluid communication with the first fluid conducting means;

(B) a second microcolumnar section having a center line, an inlet end portion having an inlet end, and a lumen for conducting a fluid flow, the second microcolumnar section being operatively connected and in fluid communication with the microcolumn of the second fluid conducting means; and (C) a channel having a center line and inwardly facing wall and enclosing at least a portion of the first microcolumnar section and at least a portion of the second microcolumnar section for conducting a flush fluid flow past said ends of the microcolumnar sections, the inwardly facing wall of the channel nonfixedly constraining and aligning said end portions of the first and second microcolumnar sections, due to the relative curvature and elasticity of the microcolumnar sections and the channel, such that said outlet end of the first microcolumnar section is proximate said inlet end of the second microcolumnar section and such that the center lines of said outlet end portion and said inlet end portion are generally parallel to facilitate the transfer of fluid from said outlet end of first microcolumnar section to said inlet end of second microcolumnar section when desired; and (d) connecting a flush liquid supply means operatively to and in fluid communication with the channel for flowing the flush fluid through the channel.

* * * * *